United States Patent [19]
Lehmann et al.

[11] Patent Number: 5,175,285

[45] Date of Patent: Dec. 29, 1992

[54] POLYMERS DERIVED FROM POLYSUCCINIMIDE, USED AS SURFACE COATINGS FOR MEDICINALS AND FOODS

[75] Inventors: Klaus Lehmann; R iger Jelitte, both of Rossdorf; Joachim Knebel, Darmstadt, all of Fed. Rep. of Germany

[73] Assignee: Rohm GmbH Chemische Fabrik, Darmstadt, Fed. Rep. of Germany

[21] Appl. No.: 548,368

[22] Filed: Jul. 5, 1990

[30] Foreign Application Priority Data

Jul. 4, 1989 [DE] Fed. Rep. of Germany ....... 3921912

[51] Int. Cl.⁵ .................. C07D 403/04; C07D 401/04; C07D 413/04; C08G 9/24
[52] U.S. Cl. .................................. 544/141; 544/372; 546/275; 548/546; 548/520
[58] Field of Search ................ 548/546, 520; 544/141, 544/372; 546/275

[56] References Cited

U.S. PATENT DOCUMENTS 4,483,807  11/1984  Asano et al. .
4,906,473  3/1990   Bader et al. .
5,041,291  8/1991   Bader et al. .

FOREIGN PATENT DOCUMENTS 3612102  10/1986  Fed. Rep. of Germany .
3700128  10/1986  Fed. Rep. of Germany .
2175596  6/1989   United Kingdom .

OTHER PUBLICATIONS

*Journal of Medicinal Chemistry*, 1973, vol. 16, No. 8, pp. 893-897.
Chemical Abstracts, vol. 107, 1987 pp. 492-493.

*Primary Examiner*—David B. Springer
*Attorney, Agent, or Firm*—Oblon, Spivak, McClelland, Maier & Neustadt

[57] ABSTRACT

A conversion product of polysuccinimide useful as coating material for medicinal preparations and foodstuffs having the structure:

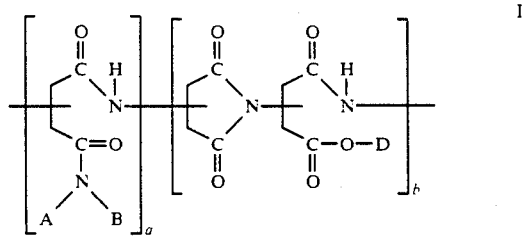

wherein
A is hydrogen or a straight or branched alkyl or alkylene group of 1 to 8 carbon atoms, optionally substituted by cycloaliphatic or aromatic groups, wherein the cyclic substituent can also contain heteroatoms, or by R—O—,

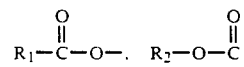

or $R_3R_4N$ groups, wherein R, $R_1$, $R_2$, $R_3$, and $R_4$ are hydrogen or branched alkyl or cycloalkyl groups each of which may contain oxygen and nitrogen atoms in the chain or in the ring of 1 to 10 carbon atoms;
B is hydrogen or straight or branched chain alkyl or alkenyl, and is the same or different from A;
D is hydrogen, $NH_4$.

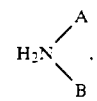

wherein A and B have the aforementioned meanings, or an alkali metal ion; and
a is 0.2 to 1 and b is 0.8 to 0.

6 Claims, No Drawings

POLYMERS DERIVED FROM POLYSUCCINIMIDE, USED AS SURFACE COATINGS FOR MEDICINALS AND FOODS

BACKGROUND OF THE INVENTION

1. Field of the Invention

The invention relates to biologically compatible polyaspartic acid derivatives and their application primarily for pharmaceutical and food preparations.

2. Description of the Background

Polymeric substances are used on a large scale in both the pharmaceutical technology and food technology. In these applications these substances are in themselves not drugs or foods but rather are indispensable for specific applications of the active ingredients or for, e.g., the special processing of foods.

Polymeric, film-forming substances are, for example, used to improve the handling of pharmaceutical preparations, to improve their storage stability and, above all, to influence the rate of release of the active substances during their medicinal application. Synthetic polymers and chemically modified natural substances such as polyethylene glycol, polyvinylpyrrolidone, polymethacrylates, polyvinyl acetates and cellulose ester and cellulose ether are used.

A number of synthetically manufactured polypeptides already exist for special applications in medicine and pharmacy. Apart from peptides with effect-specific sequence, there are also polymers from individual amino acids such as primarily polyaspartic acid, polyglutamic acid and polylysine, and copolymerizates of monomer components on which these polyamino acids are based. These polymers have no special biological efficacies and have been proposed as plasma expanders.

Derivatives of such polyamino acids are also known and are biologically quite compatible. Thus, α-β-poly(2-hydroxyethyl)-DL-aspartamide can be employed as a plasma expander (P. Neri et al., Journal of Medicinal Chemistry, 1973, Vol 16, pages 893-897). Acyl derivatives of α-β-poly(2-hydroxyethyl)-DL-aspartamide and, in general, of α,β-poly-(hydroxyalkyl)-DL-aspartamides are described in DE-OS 37 00 128. By building in suitable biologically inactive acyl groups the decomposition rate of these polymers can be controlled in vivo in the desired manner. Thus, they are suitable for incorporating decomposable drug implants with controlled release of the active substances. The active substances are embedded in the polymer matrix.

Soluble and biologically degradable copolymerizates from aspartic acid and/or glutamic acid units, which contain reactive groups such as, e.g., hydrazide or azide groups, for the chemical bonding of biologically active substances are known from DE-OS 36 12 102.

In order to achieve a targeted release of active substances to or in the vicinity of their sites of action, drugs are administered a multiple number of times in the form of coated tablets. All previously known polyamino acids and their derivatives have not yet been used as surface coatings for medicinal forms and also for foods despite the foreseeable advantages. This can be justified by the cost or the reason can lie in the properties of polyamino acids and their derivatives that are known to date. Thus, the prior art α, β-poly-(2-hydroxyethyl)-DL-aspartamide is too hydrophilic for the field of application of coatings for medicinal preparations and foodstuffs.

SUMMARY OF THE INVENTION

Accordingly, one object of the present invention is to provide biologically compatible polymers that are built up of natural components which form films and which can be used to manufacture surface coatings for pharmaceutical and food preparations, said films capable of being prepared cost-effectively from low molecular weight substances that are readily obtainable.

Briefly, this object and other objects of the present invention as hereinafter will become more readily apparent and can be attained in a conversion product of polysuccinimide having the structure:

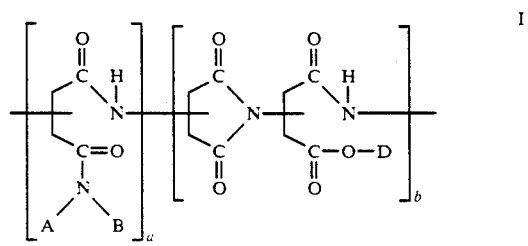

wherein

A is hydrogen or a straight or branched alkyl or alkylene group of 1 to 8 carbon atoms, optionally substituted by cycloaliphatic or aromatic groups, wherein the cyclic substituent can also contain heteroatoms, or by R—O—,

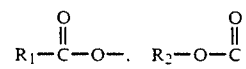

or $R_3R_4N$ groups, wherein R, $R_1$, $R_2$, $R_3$, and $R_4$ are hydrogen or branched alkyl or cycloalkyl groups each of which may contain oxygen and nitrogen atoms in the chain or in the ring of 1 to 10 carbon atoms;

B is hydrogen or straight or branched chain alkyl or alkenyl, and is the same or different from A;

D is hydrogen,

wherein A and B have the aforementioned meanings, or an alkali metal ion; and a is 0.2 to 1 and
b is 0.8 to 0.

DETAILED DESCRIPTION OF THE PREFERRED EMBODIMENTS

It has now been found that synthetic polymers formed of aspartic acid units, which are obtained by ring opening resulting by reaction of polysuccinimide with compounds of the formula 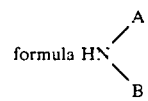

in which A and B are hydrogen and/or organic groups from alkyl or alkylene groups, which can contain still other functional groups, are suitable for coating foodstuffs and medicinal preparations, and that their specific solubility under the conditions of application can be adjusted through the functional groups of the retarding agents of the invention. As film-forming substances, the present polypeptides, built up of naturally occurring amino acids, have advantages because of their good biological compatibility and because of the physiological safety of the starting materials used to manufacture them, so that consumers, primarily ill patients, do not suffer from their consumption. The chemical and physical properties of the polypeptide coating substance are essentially the decisive factors in the use of various medicinal preparations such as tablets, in particular the decomposition properties of the coating/substance in water and in the digestive juices of the stomach or the intestine, as these decomposition characteristics affect the rate of release of active substance.

The polymers of the present invention have molecular weights ranging from 10,000 to 200,000, preferably ranging from 30,000 to 150,000. They are suitable for the manufacture of coatings of medicinal preparations that retard deterioration of the preparations. The polymers have a specific effect as surface coatings for foodstuffs and nonessential consumables.

Drugs and foodstuffs can be coated with the polymers of the present invention, thus protecting them against the external environment during the manufacture and storage of such products. Further, the products are protected from handling by consumers but upon ingestion, permit release of the active substances therein in the intestinal tract. Depending on the nature of the functional groups on the polymers and the resulting solubility properties of the polymers, the polymer films retard dissolution, and delay release of the coated products, thereby providing release of active substance by diffusion or by a pH dependent release. As long as the films are insoluble in the medium of the intestinal tract, they also protect the enveloped active substance from undesired reactions. Thus, e.g., bitter tasting drugs can be retained in the neutral milieu of the saliva and quickly released in the acidic gastric juice; substances that irritate the stomach or are sensitive to acid are enveloped by a film that is stable with respect to gastric juices and are not released until the intestinal juices change to a pH above 6, while other specific active substances are not released until the colon is reached where the pH is above pH 7. Thus, side effects can be avoided and therapeutic actions can be improved. The coating polymers dissolve in the anticipated milieu and are eliminated through the natural metabolic pathways. By using polymers that are almost natural as a surface coating for drugs, the stress from exogenous materials and the risk of allergic and toxic reactions in patients is reduced.

For application in the food sector, e.g., to envelop foods and non-essential consumables and the like, the polymer can be used in an advantageous manner as a material which is glucose free thereby preventing dental cavity formation during consumption of the food.

The polysuccinimide which is used for the preparation of the polyaspartic acid derivatives of the present invention can be synthesized by known methods, e.g., according to the method described by P. Neri et al. in J. Med. Chem. 16, 893 (1973), through polycondensation of aspartic acid in the presence of phosphoric acid. Polysuccinimide that is obtained in this manner and which can also be called polyanhydroaspartic acid has a molecular weight of about 100,000 (determined by means of viscosimetry, see Neri et al) which is a relatively high molecular weight. According to the known manufacturing methods, which are disclosed by Neri, polysuccinimides with molecular weights ranging from 10,000 to 200,000 can be obtained that are suitable for reaction with amines

to form the film-forming polyaspartic acid derivatives of the present invention.

The polyaspartic acid derivatives of the present invention are obtained from polysuccinimide and one or more amines of the formula:

wherein A is H or an alkyl group or an alkylene group of 1 to 8 carbon atoms, which can be branched and which can be substituted with cycloaliphatic or aromatic groups, wherein the ring-shaped substituent can also contain heteroatoms, or R—O—,

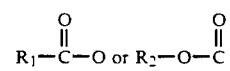

or $R_3$, $R_4N$ groups, wherein R, $R_1$, $R_2$, $R_3$, and $R_4$ can be H or if desired, branched alkyl groups or cycloalkyl groups which may contain oxygen or nitrogen atoms in the chain or in the ring, with 1 to 10 carbon atoms*); and B is H or an alkyl or alkylene group as defined under A and which can be the same as or different from A.

*) The minimum ring size being 3 carbon atoms.

Suitable examples of the amine includes ammonia and the following amines: methylamine, butylamine, hexylamine, ethanolamine, neopentanolamine, 3-isononyloxypropylamine, 3-propanolamine, 2-methoxyethylamine, 3-methoxypropylamine, 3-ethoxylpropylamine, tetrahydrofurfurylamine, furfurylamine, benzylamine, 2-methoxybenzylamine, tyramine, ethylhexoxypropylamine, monoisopropanolamine, diethanolamine, diisopropanolamine, 5-amino-1-pentanol, 4-aminocyclohexanol, 2-aminophenylethanol-1, 1-(2-aminoethyl)piperazine, N,N-dimethyl-1,3-propanediamine, 2-aminopyridine, 3-aminopyridine, 4-aminopyridine, N-(3-aminopropyl)pyrrolidone, morpholinoethylamine, glycine ethyl ester (from these or similar esters through hydrolysis of the carboxylic acid derivatives) and other amino acids and their derivatives.

The reaction of polysuccinimide with amines can be carried out as described by Neri (see also, P. Neri, G. Antoni, Macromol. Synth. 8, 25) in a mild manner at relatively low temperatures, i.e., at temperatures below 60° C., usually about 20° C., in order to avoid disintegration of the polymer chain. In order to adjust the properties of the polymers to be used as surface coatings, it has been found to be expedient to conduct the analogous polymer conversion in the range of 30 to 100 mole %, especially in the range of 30 to 100 mole %, and, above all, in the range of 50 to 95 mole % of the succinimide structural units. In addition, for each mole of polysuccinimide, 0.2 to 1 mole of one or more amines

are reacted, wherein polymers with 20 to 100 mole % of α,β-D,L-aspartamide units and 80 to 0 mole % of D,L-succinimide units are obtained. To obtain a nearly 100% degree of derivatization, the conversion is conducted preferably in the presence of about 10 to 200 mole % of excess amine.

The conversion is conducted normally in the presence of an inert, polar, aprotic solvent, for example, in dimethylacetamide, in dimethylsulfoxide or preferably in dimethylformamide. However, it is not necessary to use a solvent such as in the reaction of ethanolamine or isopropanolamine with polysuccinimide where the polymer is reacted directly with the amine.

If water is present during or following the reaction of the polysuccinimide with the amine

the resulting polymer containing aspartic acid components, as noted in formula I can exist in protonated form or in the form of salt, or can be put into one of these forms.

The purification of polymeric aspartic acid derivatives, in particular the separation of the polymer from solvents that are otherwise difficult to remove and unconverted amine, can be conducted by precipitating said polymer derivatives from methanol solutions as acetone or isopropanol is introduced therein.

For the anticipated application as a surface coating material, especially as a coating which retards object degradation, the solubility properties of the polyaspartic acid derivatives of the invention can be influenced, above all, by the structure of the

side groups. Thus, e.g., derivatives, which are prepared with isopropanolamine or with neopentanolamine, exhibit good solubility in alcohols or water, or, following the addition of 10 to 20% by weight of water, the derivatives that are obtained with glycine ester or tetrahydrofurfurylamine also exhibit good alcohol solubility. Derivatives that bear, for example, amino groups in the side chains are quite soluble in diluted acids and, thus, also, in gastric juice. Thus, with the surface coatings prepared according to the invention, the release of the active substance from products manufactured with it can be targeted for specific environments.

The polyaspartic acid derivatives of formula I are quite suitable for coating medicinal preparations or foodstuffs or non-essential consumables such as coffee, tea, cigarettes, and the like, etc., or for the separate manufacture of coatings or wrappings such as capsules or films for products from the drug, food and consumable sectors.

The degradation retarding coating material for medicinal preparations can be applied to the substrate materials according to known methods of pharmaceutical technology (Ullmanns Encyklopadie der technischen Chemie, 4th edition, volume 18, pages 151 to 161) from a solvent or from a dispersion with film formation. Substrate materials are all solid drugs such as tablets, coated tablets, pills, granulates, pellets, crystals, powder and capsules. Capsules manufactured from polyaspartic acid derivatives as such are available for subsequent filling with, e.g., pharmacological substances. For local and transdermal treatments on the skin, films and foils made of polyaspartic acid amide derivatives with active substances such as dithranol, can be manufactured, e.g., through web pouring.

Foods and non-essential consumables which can be coated in accordance with the invention, are, for example, sausages and meat products, cheese, candy, confectionery, chewing gum, and the like. For instance, chewing gum coatings can be obtained largely sugar-free and are very stable in automatic vending machines.

Examples of coating methods which can be used include the likes of the pan coating procedure and the fluid bed coating procedure which are particularly useful in pharmaceutical preparations. Also the new surface coating technique can be used which simultaneously coats and granulates powders. Granulates are obtained which can be compressed to matrix tablets or filled into capsules. Also those made of polyaspartic acid amide derivatives.

Substrates, above all those having larger dimensions which are more customary in the food sector, can also be coated in accordance with the invention by submerging substrates in the polymer or by pouring solutions, dispersions or melts of polymers of formula I on the substrates. Still further, substrates can be sealed into films that are manufactured separately according to prior art techniques (Ullmann, 4th edition, volume 11, pages 673 to 677) and are made of polyaspartic acid amides with thicknesses ranging from about 50 to 1,000 μm.

When the polymer of the invention is employed as a coating for drugs, the surface coating which results generally has a thickness ranging from 5 to 50 μm, primarily a layer thickness ranging from 10 to 30 μm. To coat granules and smaller particles, this corresponds to a varnish coating ranging from about 10 to 20% by weight. For tablets, coated tablets, and capsules, the thickness corresponds to a varnish coating ranging from about 3 to 5% by weight, based on the weight of the coated core.

Suitable additives which can be formulated in the coating material of the invention for the uses stated above include, if necessary, additives such as preservatives, dyes and pigments, softeners and releasing agents.

For coating, the polymers of formula I are used as about 5 to 25%, especially as 10 to 20% solutions, in solvents such as methanol, isopropanol, acetone, water, mixtures of water and alcohol, if necessary, in the presence of dissolved or suspended additives. The polymers are also used in the form of film-forming dispersions, preferably primarily as aqueous dispersions, to manufacture the surface coatings. The dispersions can be obtained by adding precipitating agents to solutions of polyaspartic acid derivatives such as water to solutions in organic solvents, or such as organic precipitating agents to aqueous solutions. Dispersions for the use of the polymers I of the invention to prepare retardant-acting surface coatings can also be obtained by dispersing polymer powders such as during concentration of polymer solutions by evaporation or through precipitation from solutions.

Having generally described this invention, a further understanding can be obtained by reference to certain specific examples which are provided therein for purposes of illustration only and are not intended to be limiting unless otherwise specified.

A. Preparation of the Polymers

In Examples 2 to 10, the aspartamide units have the formula:

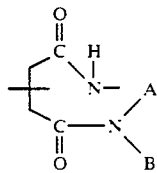

EXAMPLE 1

A 50 g amount of aspartic acid is mixed with 25 g of 85% phosphoric acid to a homogeneous mass in a 1 liter round-bottom flask. The flask is connected to a rotary evaporator and evacuated to 100 mbar. With the rotary evaporator running, the reaction mixture is held for 3 hours at 180° C. in a preheated oil bath. Then it is left to cool. The reaction product is suspended and washed with water free of acid on a sintered glass suction filter. The product is dried at 80° C. in vacuum. It is identified as polysuccinimide by means of IR and NMR spectroscopy.

Yield: 35.5 g = 97.3 % of the theoretical.

| Elemental analysis: | calc.: | 49.5% C | 3.1% H | 14.4% N |
|---|---|---|---|---|
| | found: | 46.5% C | 3.7% H | 13.5% N |

Molecular weight, by means of viscosimetry in DMF, according to Neri et al. in J. Med. Chem. 16, page 894 (1973): 90,000.

EXAMPLE 2

α,β-D,L-poly(isopropanol)aspartamide
A = H
B = —CH$_2$—CHOH—CH$_3$

Five grams of (51 mmol) polysuccinimide are dissolved in 30 ml of DMF. 20 ml (0.93 mol) of isopropanolamine is added drop-by-drop to the solution. The mixture is stirred for 24 hours at room temperature. Then the reaction mixture is introduced into a five-fold volume of acetone. The precipitated product which forms is drawn off and washed well with acetone. Subsequently, it is dissolved in 20 ml of methanol and precipitated again in an excess of acetone. The product is thoroughly washed with acetone and dried at 60° C. in vacuum. Yield 5 g = 56% of the theoretical. The structure is confirmed by IR and NMR spectroscopy.

Mole quantity: 14,700 (confirmed by GPC, standard polyacrylic acid)

| Elemental analysis: | calc.: | 48.83% C | 7.02% H | 16.27% N |
|---|---|---|---|---|
| | found: | 46.3% C | 7.5% H | 15.2% N |

EXAMPLE 3

α,β-D,L-poly(diisopropanol)aspartamide
A and B = —CH$_2$—CHOH—CH$_3$

The procedure of Example 2 is employed except that 66 g (0.68 mol) of polysuccinimide, 250 ml DMF and 90.5 g (0.68 mol) of diisopropanolamine are employed.

Yield: 89 g = 57% of the theoretical
Mole quantity: 22,600 (GPC, standard polyacrylic acid)

| Elemental analysis: | calc.: | 52.16% C | 7.88% H | 12.17% N |
|---|---|---|---|---|
| | found: | 49.1% C | 6.5% H | 12.4% N |

EXAMPLE 4

α,β-D,L-poly(3-ethoxypropyl)aspartamide
A = H
B = —CH$_2$—CH$_2$—CH$_2$—OC$_2$H$_5$ The procedure of Example 2 is repeated except that 20 g (0.2 mol) of polysuccinimide, 50 ml of DMF and 55 g of (0.625 mol) of 3-ethoxypropylamine are used.

Yield: 37 g = 97% of the theoretical of slightly yellowish colored solid.

Structure confirmed by IR and NMR.

| Elemental analysis: | calc.: | 53.99% C | 8.05% H | 13.99% N |
|---|---|---|---|---|
| | found: | 51.9% C | 8.3% H | 13.4% N |

EXAMPLE 5

α,β-D,L-poly(3-ethoxypropyl)aspartamide
A = H
B = —CH$_2$—CH$_2$—CH$_2$—OCH$_3$

The procedure of Example 2 is repeated except that 30 g (0.31 mol) of polysuccinimide, 20 ml of DMF and 100 g (1.33 mol) of methoxyethylamine are used.

Yield: 27 g = 51% of the theoretical of slightly yellowish colored solid.

Structure confirmed by IR and NMR.

| Elemental analysis: | calc.: | 49.33% C | 7.02% H | 16.27% N |
|---|---|---|---|---|
| | found: | 46.6% C | 7.4% H | 14.8% N |

EXAMPLE 6

α,β-D,L-poly(hydroxyethyl)aspartamide-co-succinimide (1:1)
A = H
B = —CH$_2$—CH$_2$OH The procedure of Example 2 is repeated except that 5 g (51 mmol) of polysuccinimide, 30 ml of DMF and 1.6 g (25.7 mmol) of ethanolamine are used.

Reaction time: 1 hour at room temperature
Yield: 6.5 g = 98% of the theoretical of a colorless solid. Hydroxyethylaspartamide and succinimide units can be detected in the NMR spectrum.

molar ratio: 1:1

| Elemental analysis: | calc.: | 47.06% C | 5.09% H | 16.46% N |
| --- | --- | --- | --- | --- |
| | found: | 44.2% C | 5.3% H | 15.4% N |

EXAMPLE 7

α,β-D,L-poly(diisopropanol)aspartamide-co-succinimide (1:1) A and B=—CH$_2$—CHOH—CH$_3$ The procedure of Example 2 is repeated except that 10 g (103 mmol) of polysuccinimide, 30 ml of DMF and 6.86 g (51.5 mmol) of diisopropanolamine are used.

Yield: 14.2 g=84.2% of the theoretical of a colorless solid.

Diisopropanolaspartamide and succinimide units can be detected in the NMR spectrum.

Molar ratio: 1:1

| Elemental analysis: | calc.: | 51.38% C | 6.42% H | 12.84% N |
| --- | --- | --- | --- | --- |
| | found: | 48.5% C | 5.6% H | 13.0% N |

EXAMPLE 8

α,β-D,L-polyasparagine
A and B=H

Ten grams (103 mmol) of polysuccinimide are dissolved in portions in 200 ml of 25% aqueous ammonia solution and stirred for 1.5 hours at room temperature. Then, the product is precipitated in 1 liter of acetone and isolated by centrifuging. Eleven grams (93.6% of the theoretical) of a slightly yellowish colored compound, which is dried in vacuum at 80° C., are obtained. The structure is confirmed by NMR spectroscopy.

Molar quantity: 13,400 (GPC, standard polyacrylic acid)

| Elemental analysis: | calc.: | 42.11% C | 5.3% H | 24.55% N |
| --- | --- | --- | --- | --- |
| | found: | 38.6% C | 5.8% H | 20.3% N |

EXAMPLE 9

α,β-D,L-poly(tetrahydrofurfurylmethyl)aspartamide
A=H

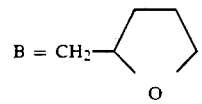

B = CH$_2$—

The procedure of Example 2 is repeated except that 90 g (0.93 mol) of polysuccinimide, 150 ml DMF and 100 g (0.99 mol) of tetrahydrofurfurylmethylamine are used. In addition, the product is dissolved in 200 ml of methanol and precipitated in an excess of acetone. Following washing with acetone and drying in vacuum, 26 g (13% of the theoretical) of poly(tetrahydrofurfurylmethyl)aspartamide are obtained in the form of a slightly yellowish colored solid. The structure is confirmed through IR and NMR spectroscopy.

| Elemental analysis: | calc.: | 54.55% C | 7.07% H | 14.14% N |
| --- | --- | --- | --- | --- |
| | found: | 53.7% C | 7.8% H | 12.4% N |

EXAMPLE 10

α,β-D,L-poly(isononyloxypropyl)aspartamide
A=H
B=CH$_2$—CH$_2$—CH$_2$—OC$_9$H$_{19}$ The procedure of Example 2 is repeated except that 5 g (51 mmol) of polysuccinimide, 40 ml of DMF and 20 g (100 mmol) of isononyloxypropylamine are used.

The product is obtained by introducing the reaction mixture into five times the volume of water, washed with water, reabsorbed in 20 ml DMF and precipitated in an excess of water. After being thoroughly washed with the precipitating agent, the product is dried to a constant weight in vacuo at 60° C. A 6.2 g amount (40.4% of the theoretical) of a slightly yellowish colored solid are obtained. The structure is confirmed through NMR spectroscopy.

Molar quantity: 38,400 (GPC, standard: polymethylmethacrylate)

| Elemental analysis: | calc.: | 64.43% C | 10.1% H | 9.4% N |
| --- | --- | --- | --- | --- |
| | found: | 62.1% C | 10.1% H | 9.4% N |

B. Application of the Polymers as surface coating agent

Example A

Fast decomposing coating on tablets 120 g amount of tablets with a diameter of 10 mm, a total thickness of 4.3 mm and a weight of 350 mg per unit were coated as they were rotated in a small coating pan having a 14 cm diameter with a solution of 2.7 g of poly(isopropanol) aspartamide, according to Example A2, in 23 g of methanol. In addition, small portions of about 0.1-0.2 ml were trickled onto the rotating tablet cores and, following a brief distribution, by blowing in a warm air current of about 50° C., were dried. The result was a glossy, dust-free coating, which feels slightly sticky, but the tablets do not adhere to one another when stored in a sealed glass. The tablets disintegrate in a disintegration tester according to DAB in water, in synthetic gastric juice (0.1N HCl), and also in synthetic intestinal juice with a pH of 6.8 within less than 3 minutes and completely release within 30 minutes the quinidine sulfate that is contained as the active substance.

Example B

Colored surface film coating on tablets

A 2.0 g amount of poly(diisopropanol)aspartamide, prepared according to Example A3, was dissolved in 8-10 g of water and mixed in an aqueous pigment suspension, which contained 12% talcum, 4% titanium dioxide, 4% yellowish orange varnish E 110, 3.6% Of polyethylene glycol 6000, 2.4% of polysorbate (®) Tween 80) and 16% of lactose. The mixture was added, as in Example 1, in small portions to 120 g of tablets having identical dimensions and rotating in the coating pan and were dried by blowing in warm air with a hot air blower. The brightly shining, coated tablets are dust-free and free-flowing; they feel smooth and do not stick and disintegrate in water, synthetic gastric juice and synthetic intestinal juice within a maximum of 3 minutes. The active substance—quinidine sulfate—that is contained therein is completely released within 30 minutes.

Example C

A 5 g amount of poly(isopropanol)aspartamide was dissolved in 95 g of methanol and was sprayed an 500 g of tablets, which rotate in a coating pan having a diameter of 25 cm. The tablets had a diameter of 10 mm and a total thickness of 3 mm; the weight was 300 mg per unit. A pneumatic spray gun—Walther WA I—whose nozzles have a 1.0 mm diameter was used to spray the tablets. The distance to the tablets rotating in the coating pan was 8-10 cm. The drying was done with a hot air blower with an output of 0.45 m³ per minute at an inlet air temperature of 50° C. Continuous spraying was possible with the coating pan revolving at 30 rpm and the pan tilted at 30° at a spraying pressure of 0.05 bar and at a product temperature of 33° C. The spraying period was a total of 28 min. The coated tablets were after-dried at 40° C. for 2 hours. The result was a smooth, uniform, dull shining surface coating. The film coating exhibited a taste modifying effect. No bitter taste could be perceived when the tablet was sucked for more than at least 10 sec. The tablets disintegrated in water and synthetic gastric juice within a maximum of 1 minute. The coated tablet's hardness and the resistance to abrasion was significantly higher than the uncoated starting material.

Example D

Film coating on pellets

Onto a fluid bed device (Glatt WSG 5) hot air was blown from the bottom through 5 kg of pellets having a diameter ranging from 0.5-1.22 mm and having an 8% chlorophenamine maleate content. At this stage a solution of 125 g of poly(diisopropanol)aspartamide in 1,152 g of water was sprayed onto the pellets with a pneumatic spray gun, which was fixed in position in the upper section of the fluid bed. In this process the temperature of the inlet air was held at about 40-45° C. and, at the start of any inclination of the cores towards agglomeration, the spraying was intermittently interrupted for a short period of time. After 46 minutes, the total quantity was sprayed on and the material was after-dried at 40° C. overnight. The pellets were free-flowing and dust-free.

Example E

A 2 kg amount of pellets with a diameter of 0.8-1.5 mm were swirled in a fluidized bed device (Glatt GPC 6 1) with a screen filter insert in a hot air current ranging from 43°-45° C. 50 g of poly(isononyloxypropyl)aspartamide were dissolved in 450 g of water and mixed with 500 g of a pigment suspension comprising 85 g of talcum, 25% of titanium oxide, 25 g of quinoline yellow varnish, 15 g of polyethylene glycol 6,000 and 205 g of water and sprayed in the hot air current under constant swirling over 70 minutes. The nozzle diameter was 1.2 mm and the spray suspension was metered from a supply vessel by means of a hose pump of the nozzle. After drying, 16 hours at 40° C. in the circulating air drying cabinet, the pellets showed a colorful, dull shining coating. The chlorophenamine maleate obtained thus was released with a delayed action in a release test - dissolution test in accordance with USP XXI, apparatus 2 (paddle method) within 1 -2 hours.

Example F

A 2 kg amount of theophylline powder was made moist in a 5 liter VA vessel while stirring with a solution comprising 10 g of poly(ethoxypropyl)aspartamide (see example A4 for preparation) in a mixture comprising 40 g of ethanol and 60 g of water while stirring and forced through a sieve having 2 mm clear mesh size. After drying, a granulate is obtained that was mixed with 1% of magnesium stearate and compressed on a tablet press to blanks with a diameter of 10 mm and a thickness of 3.5 mm. To this end, 15 kN compressed air was necessary; and the tablets showed a breaking strength of 120N. Then the tablets were tested in a release test in accordance with USP (paddle device; see Example 5), in which test the active substance within the tablets was delayed in its release over a period of 2 to 3 hours.

Example G

A 13 g amount of spherical chewing gum blanks with a diameter of 15 mm were moved in a coating pan with a diameter of about 25 cm at a speed of 15 rpm and sprayed with a solution of 30 g of poly(tetrahydrofurfurylmethyl)aspartamide (see example A9 for preparation), in which 10 g of talcum are also suspended in a mixture comprising 240 g of acetone and 60 g of water. During the spraying process, which was conducted with a pneumatic spray gun having a nozzle diameter of 1.0 mm, the drying air that was blown in was held at a temperature of about 30° C. After a total spraying period of 60 minutes and an after-drying of 5 minutes in the air current of the same temperature, the result was lustrous blanks, which were free of dust and stable with respect to handling and also did not stick together in storage vessels at 30° C.

Example H

Manufacture of matrix tablets

A 600 g amount of water-free theophylline granulate having a grain size ranging from 0.3-0.8 mm was mixed with 228 g of calcium hydrogen phosphate (Emcompress) and 150 g of poly(isononyloxypropyl)aspartamide, manufacturing example A10, wherein the polymer had been previously ground to a grain size below 0.1 mm. The theophylline granulate, calcium hydrogen phosphate and the polymer were, first of all, premixed in the tumble mixer and subsequently pressed through a sieve having a clear mesh size of 1 mm. Following the addition of 15 g of talcum and 7 g of magnesium stearate, this premixture was moved for another 15 minutes in the tumble mixer and compressed in an eccentric press at a pressure ranging from 15 to 20 kN into tablets with a 12 mm diameter and a radius of curvature of 25 mm. The breaking strength was 100N. In the release test in accordance with USP (paddle method; see Example 5) the tablets release with slow disintegration more than 80% of the active substance within four hours.

Having now fully described the invention, it will be apparent to one of ordinary skill in the art that many changes and modifications can be made thereto without departing from the spirit or scope of the invention as set forth herein.

What is claimed as new and desired to be secured by Letters Patent of the United States is:

1. A polymer useful as coating material for medicinal preparations and foodstuffs prepared from a polysuccinimide having the structure:

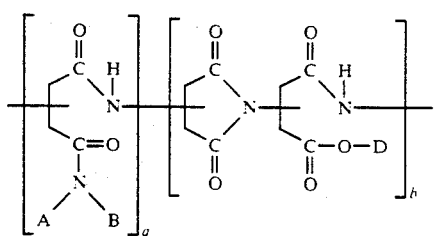

wherein the radical

in the polysuccinimide is derived from ammonia or an amine selected from the group consisting of methylamine, butylamine, hexylamine, ethanolamine, neopentanolamine, 3-isononyloxypropylamine, 3-propanolamine, 2-methoxyethylamine, 3-methoxypropylamine, 3-ethoxylpropylamine, tetrahydrofurfurylamine, furfurylamine, benzylamine, 2-methoxybenzylamine, tyramine, ethylhexoxypropylamine, monoisoprpanolamine, diethanolamine, diisopropanolamine, 5-amino-1-pentanol, 4-aminocyclohexanol, 2-aminophenylethanol-1, 1-(2-aminoethyl)piperazine, N,N-dimethyl-1,3-propanediamine, 2-aminopyridine, 3-aminopyridine, 4-aminopyridine, N-(3-aminopropyl)pyrrolidone, morpholinoethylamine and glycine ethyl ester; D is hydrogen, NH$_4$.

wherein radical

is as defined above, or an alkali metal ion; and a is 0.2 to 1 and b is 0.8 to 0.

2. The polymer of claim 7, wherein 30 to 100% of the succinimide structural units are converted into aspartic acid amide units.

3. The polymer of claim 2, wherein 50 to 95% of the succinimide structural units are converted into asparatic acid amide units.

4. The polymer of claim 1, which is obtained by reacting polysuccinimide with isopropanolamine and/or diisopropanolamine.

5. The polymer of claim 1, which is obtained by reacting polysuccinimide with 3-ethoxypropylamine.

6. The polymer of claim 1, which is obtained by reacting polysuccinimide with isononyloxypropylamine.

* * * * *

UNITED STATES PATENT AND TRADEMARK OFFICE
CERTIFICATE OF CORRECTION

PATENT NO. : 5,175,285

DATED : December 29, 1992

INVENTOR(S) : Klaus Lehmann et al.

It is certified that error appears in the above-identified patent and that said Letters Patent is hereby corrected as shown below:

On the title page, Item [75],

The second inventor's name is incorrect, should be, --Rudiger Jelitte--

Signed and Sealed this

Second Day of November, 1993

Attest:

BRUCE LEHMAN

Attesting Officer

Commissioner of Patents and Trademarks